(12) United States Patent
Boehm et al.

(10) Patent No.: US 9,848,991 B2
(45) Date of Patent: Dec. 26, 2017

(54) EXPANDABLE IMPLANT FOR THE SPINAL COLUMN

(71) Applicants: Heinrich Boehm, Weimar (DE); Andreas Burger, Tuttlingen (DE); Gerd Widmaier, Tuttlingen (DE); Klaus Wenzler, Frittlingen (DE)

(72) Inventors: Heinrich Boehm, Weimar (DE); Andreas Burger, Tuttlingen (DE); Gerd Widmaier, Tuttlingen (DE); Klaus Wenzler, Frittlingen (DE)

(73) Assignee: Heinrich Boehm, Weimar (DE)

( * ) Notice: Subject to any disclaimer, the term of this patent is extended or adjusted under 35 U.S.C. 154(b) by 527 days.

(21) Appl. No.: 14/335,920

(22) Filed: Jul. 20, 2014

(65) Prior Publication Data

US 2015/0025634 A1 Jan. 22, 2015

(30) Foreign Application Priority Data

Jul. 19, 2013 (DE) .......................... 10 2013 107 723

(51) Int. Cl.
*A61F 2/00* (2006.01)
*A61F 2/44* (2006.01)
(Continued)

(52) U.S. Cl.
CPC ............ *A61F 2/4425* (2013.01); *A61F 2/442* (2013.01); *A61F 2/4465* (2013.01); *A61F 2/4611* (2013.01); *A61F 2002/2835* (2013.01); *A61F 2002/3041* (2013.01); *A61F 2002/30411* (2013.01); *A61F 2002/30525* (2013.01); *A61F 2002/30542* (2013.01); *A61F 2002/30556* (2013.01); *A61F 2002/30579* (2013.01); *A61F 2002/30601* (2013.01); *A61F 2002/30779* (2013.01); *A61F 2002/30843* (2013.01); *A61F 2002/4475* (2013.01);
(Continued)

(58) Field of Classification Search
CPC ...... A61F 2/4611; A61F 2/4455; A61F 2/446; A61F 2/4465
See application file for complete search history.

(56) References Cited

U.S. PATENT DOCUMENTS

| | | | |
|---|---|---|---|
| 5,236,460 | A | 8/1993 | Barber |
| 8,303,663 | B2 | 11/2012 | Jimenez et al. |

(Continued)

FOREIGN PATENT DOCUMENTS

| | | |
|---|---|---|
| DE | 102011002076 A1 | 10/2012 |
| EP | 1415622 A1 | 5/2004 |

(Continued)

*Primary Examiner* — Matthew Lawson
(74) *Attorney, Agent, or Firm* — Kriegsman & Kriegsman (57) ABSTRACT

The invention relates to an expandable implant (11) with an upper plate (12) and a lower plate (16) which extend in the xy plane, which serve for anchoring on/in the vertebral support surfaces, and at least three gears (20, 25, 30) which are coupled to each other, wherein the gears (20, 25, 30) serve to expand the implant (11), and each gear (20, 25, 30) has a threaded spindle (21, 25, 31) and a threaded sleeve with corresponding inner thread (22, 27, 32), wherein the pitch of one thread (31, 32) is different from the pitch of the other threads (21, 22; 26, 27). The invention also relates to an operating instrument (80) for this implant.

8 Claims, 8 Drawing Sheets

(51) Int. Cl.
  *A61F 2/46* (2006.01)
  *A61F 2/28* (2006.01)
  *A61F 2/30* (2006.01)

(52) U.S. Cl.
  CPC ............ *A61F 2002/4629* (2013.01); *A61F 2310/00023* (2013.01); *A61F 2310/00131* (2013.01)

(56) References Cited

U.S. PATENT DOCUMENTS

| | | | |
|---|---|---|---|
| 2005/0209698 A1* | 9/2005 | Gordon | A61B 17/7005 623/17.15 |
| 2006/0069436 A1 | 3/2006 | Sutton et al. | |
| 2011/0160861 A1 | 6/2011 | Jimenez et al. | |
| 2011/0172716 A1* | 7/2011 | Glerum | A61F 2/442 606/279 |
| 2012/0179255 A1 | 7/2012 | DeFalco et al. | |
| 2012/0323329 A1* | 12/2012 | Jimenez | F16H 25/2056 623/17.16 |
| 2014/0288652 A1* | 9/2014 | Boehm | A61F 2/4465 623/17.15 |

FOREIGN PATENT DOCUMENTS

| | | |
|---|---|---|
| EP | 2476396 A1 | 7/2012 |
| WO | 2009064787 A2 | 5/2009 |
| WO | 2011011609 A2 | 1/2011 |
| WO | 2011011626 A2 | 1/2011 |

\* cited by examiner

EXPANDABLE IMPLANT FOR THE SPINAL COLUMN

The present invention relates to an expandable implant, in particular the invention relates to an expandable, height-adaptable implant for the lumbar and thoracic spine, which can serve as a replacement for vertebral bodies and/or intervertebral disc spaces in stiffening operations.

Such lumbar and thoracic implants are used for intercorporeal fusion (stiffening of the vertebral bodies). However, an intracorporeal use is also possible in principle.

In the configuration as a vertebral body replacement, the implant can be used on destroyed areas or formational defects of any kind, e.g. tumours, vertebral fractures, late sequelae following vertebral fractures, and also infections or congenital malformations of one or more vertebral bodies.

In the configuration as a partial vertebral body replacement, the implant can be used for intracorporeal use as a correction instrument and, when remaining in the body, as a reconstruction implant of a vertebral body.

In the configuration as an intersomatic cage or expandable cage, the implant can be used to restore the anterior column of the row of vertebrae in the context of stiffening procedures. Here, areas of application are degenerative diseases of the spinal column, segmental malpositioning and segmental instability of a very wide variety of causes.

Generally, the intervertebral space is first of all excavated from the back or from the direction of the thoracic or abdominal cavity; in vertebral body replacement, the vertebral body is removed and the implant is then inserted into the resulting space in order to correct the position and also to serve as a spacer for mechanically stable connection between the adjacent spinal column sections.

It has proven advantageous to design such implants in the form of a cage such that, for example, bone substance or bone replacement substances can be introduced into the interior of the cage in order to accelerate the process of incorporation. The fusion of the cage can be permitted or accelerated in this way.

Cages that can be expanded via an expansion mechanism after they have been inserted into the spinal column defect have the advantage of being able to be implanted in a technically simpler way that is gentle on the anchor vertebrae. On the one hand, the implant is firmly clamped and fixed by the stepless expansion. On the other hand, it permits individual positional corrections of the adjacent vertebrae, in order to restore normal geometric relationships by creation of lordosis of the lumbar spine or correction of an increased thoracic kyphosis.

Except in cases of malignant tumours, the aim is to allow endogenous bone tissue to grow through the implant or the reconstructed spinal column section. For this reason, such implants preferably have apertures.

Depending on their design, cages not only ensure mechanical stability of the corporectomy defect and structural integrity of the intervertebral space during the osseous fusion process, but also protect the spinal cord from moving bone fragments.

A general problem of the known implants is that the implants, after they have been fitted, are liable to sink into the adjacent vertebrae, as a result of which the position of the vertebrae relative to each other and the overall statics are disrupted. This can occur particularly in cases of reduced calcium salt content (osteoporosis) of the vertebral bodies.

Cylindrical implants are known which have a screwthread on the cylinder surface. These implants are screwed horizontally into the intervertebral space after the bottom plate and top plate of the vertebral bodies have firstly been eroded using drilling instruments, that is to say have been partially removed. A disadvantage of these cylindrical implants is that they have a relatively small bearing zone and exhibit quite considerable sinking into the vertebral bodies and become jammed.

EP 1 415 622 A1 discloses expandable implants of a more or less parallelepipedal basic shape, which have two branches which are connected to each other at one end, wherein the branches can be expanded by a slide arranged between the branches, which slide supports the branches, in the expanded state, over their entire horizontal width and locks them in the end position. Although these implants are distinguished by a larger bearing surface on the end plate of the adjacent vertebra, the nature of the expansion is very limited for design-related reasons and always predefined in terms of the angle. On account of the then often unavoidable punctiform loading, they also often sink substantially into the adjacent vertebrae and thus lose their expanding or correcting function. In addition, implantation of such cages from the side of the spinal column is not possible for design-related reasons and is limited to a strictly dorsal implantation direction or, in rare cases, strictly to an anterior implantation direction. The use as a vertebral body replacement is impossible with both of the aforementioned models.

U.S. Pat. No. 5,236,460 discloses expandable telescopic implants. The outer implant body, which is tubular, has an axial bore, in which the inner implant body is guided in a sliding movement. Plates with spikes for anchoring are provided at the upper end and lower end of the implant bodies. The expansion of the implant takes place hydraulically via a liquid or a hardenable resin. For this purpose, the outer implant body has an opening for entry of the fluid, which fluid then passes into a cavity in the lower end of the inner implant body and pushes the latter up axially in a sliding movement. A disadvantage of this is that the volume of the expansion chamber is not available for bone to grow through. The implant is screwed onto the vertebral bodies via a special bracket device, which is screwed onto the upper platform.

WO 2009/064787 discloses expandable implants with a dual telescopic adjustment mechanism, which implants have an upper plate and a lower plate for anchoring on the vertebral support surfaces. The adjustment mechanism is coupled via toothed wheels, i.e. a rotation movement is transferred from one toothed wheel to the other toothed wheel and thus from one adjustment mechanism to the other adjustment mechanism and so to the implant. According to said document, the actuation is intended to take place via a rod with a bevel gear transmission in a manner not explained in detail.

This implant is suitable as an intervertebral disc replacement and can be produced easily and cost-effectively. Moreover, on account of the larger surface of the upper and lower plates, the risk of secondary positional changes and of sinking is minimized. However, a disadvantage is that these implants have not hitherto been able to be introduced, expanded and fixed easily by a minimally invasive technique. In addition, these implants do not have the required mechanical stability, especially against shearing forces and against the bending loads that repeatedly act on the spinal column during flexion and extension of the upper body. Moreover, the design of these implants, which are expandable in parallel, has the effect that natural bone formation and growth of bone through them is made difficult, which can lead to a reduction in the long-term stability of the implant.

US 2012/017955 A1 discloses an expandable implant comprising four gears, of which two in each case are coupled to each other by toothed wheels. Above and below the toothed wheels, the gears each have a threaded spindle with a different direction of rotation, such that, when the toothed wheel is actuated, the upper thread and lower thread are unscrewed simultaneously from the upper and lower plate, and therefore the upper plate is expanded relative to the lower plate, and the implant is compressed when the threads are simultaneously screwed into the plate. The implant has a complex structure and, with a large overall volume, allows only a slight lift. This implant does not allow bone to grow through. A further disadvantage is the cylindrical shape of the implant with the circular plates that serve for anchoring on/in the vertebral support surfaces. When positioning such implants, the implant comes to lie straight in the centre of the vertebral support surface, i.e. the least hard area of the entire vertebral support surface, with the result that the implant sinks. On account of the cylindrical shape and the engagement of the operating instrument in the cylinder centre, it is also not possible, in the case of a dorsal implantation, to pivot the implant past the nerve roots and into the correct position using the operating instrument. The implant is therefore unsuitable for a dorsal, dorso-lateral or TLIF implantation.

US 2011/0160861 A1 and U.S. Pat. No. 8,303,663 B2 teach an expandable implant with a more or less rectangular basic shape and with two or three gears, respectively. The gears are coupled via a drive rod that passes through the bottom in the longitudinal direction. The insertion instrument is screwed in the longitudinal direction onto the short sides of the implant, such that the implant can be used in particular for lateral or XLIF implantation. This implant is not suitable for the TLIF technique (transforaminal/transarticular lumbar interbody fusion), since it cannot be brought round the nerve roots into the optimal position. When using the PLIF technique, this implant has to be implanted via two accesses. A further disadvantage is that the implant does not allow bone to grow through.

The object of the invention is to make available an implant which is expandable in the body and thus has a correcting function for stiffening the intervertebral space or which, after removal of vertebral bodies, serves as a replacement for vertebral bodies and adjoining intervertebral discs, and which implant is easy to handle and operate. The implant should also be able to be safely implanted using a minimally invasive technique and should permit adaptation to the desired optimal geometry of the spinal column section.

This object is achieved by an implant having the features of Claim 1 and by an operating instrument having the features of Claim 6.

According to the invention, the implant comprises an upper plate and a lower plate, and at least three gears which are coupled to each other and serve to expand the implant, and each gear has a threaded spindle and a threaded sleeve with inner thread, wherein the pitches of at least two gears, or of two threads each consisting of threaded sleeve and threaded spindle, are different.

This has the effect that, during the expansion, the plane of the upper plate is tilted relative to the plane of the lower plate, such that a corrective parallel or angular expansion of the adjoining vertebrae is achieved, i.e. a targeted and defined correction of the position of the adjacent vertebrae.

In a preferred embodiment, the gears or the threads are non-linear (in a plan view (i.e. z direction)) and instead are arranged on an arc of a circle or in the shape of a "C", i.e. two threads lie at the ends and one thread is arranged at the centre on the arc. The central thread is therefore located in the rear area (i.e. −y direction) in relation to the two end threads.

Since the pitch of the central thread pair is greater than that of the two end threads in the preferred embodiment, the rear area of the upper plate, i.e. in the region of the central thread, is lifted to a greater extent than the front area during the expansion, and therefore, with the rear edges parallel upon implantation, a lordosis shape or kyphosis correction is obtained. In principle, scoliosis corrections are also possible with a modified implantation direction or a modified thread pitch of the individual cylinders.

However, since the main use is the correction of kyphosis or reconstruction of lordosis, the effect is explained below using this example.

With respect to the upper and lower plates and the threads, the expanded implant in the lordosis shape is mirror-symmetrical to the yz plane.

By the interaction of threaded sleeve and threaded spindle, and by means of the different thread pitches, it is possible to precisely and easily set the necessary distance between the upper plate and the lower plate in the desired expansion in the lordosis shape.

Of course, the adjustment mechanism can also have more than three gears.

The three threads are coupled to each other via drive means. In a preferred embodiment, the coupling is effected by toothed wheels, which are rigidly connected to the outwardly facing curved surfaces of the threaded sleeves.

By virtue of the triple adjustment mechanism and the coupling, the expansion is initiated by three gears, and jamming of the gear is thereby avoided. Another essential advantage of the adjustment mechanism is that, as a result of the triple expansion movement, the surface area of the upper plate and lower plate is also increased, and therefore the pressure acting on the vertebral bodies per surface area element can be reduced. Compared to parallel expansion, the avoidance of punctiform introduction of force into the anchor vertebrae by angular expansion reduces the danger of undesired sinking of the implant.

For easy operation and implantation, it is also necessary that the operating instrument can be secured rigidly on the implant. For this purpose, according to the invention, the implant has means for securing, screwing or otherwise rigidly fixing the operating instrument.

The connection between implant and operating instrument must of course be releasable. Preferably, the operating instrument comprises a screwthread (outer thread), which can be screwed into a corresponding bore in the implant and which can be removed again after the positioning and expansion have been completed. However, the connection can also be made in other ways.

When the implant is secured on the operating instrument, the drive of the operating instrument is at the same time brought into engagement with one of the drive wheels of the implant. The operating instrument is preferably driven via a toothed wheel, which is driven via a further toothed wheel with a worm drive.

This design of the operating instrument permits a narrow and slender shape even in the proximal area of the instrument. This permits the minimally invasive implantation technique, e.g. via tubular retractors.

By means of a rotation movement on the handle of the gear rod, the worm drive rotates and in turn drives the further toothed wheel which, on account of the coupling, drives the toothed wheel at the proximal end of the operating element, which is brought into engagement with the toothed wheel of the implant and thus drives the toothed wheels of the implant and the three gears, which expand the implant.

According to the invention, however, the operating instrument not only allows the implant to be fixed and expanded such that a lordosis shape is achieved, it also permits a pivoting movement of the implant in relation to the handle of the operating element, i.e. allows the implant to be moved in a lateral direction relative to the (stationary) handle.

Such a pivoting movement of the implant, with the operating element stationary, allows implantation from the dorsal direction (PLIF, TLIF technique), since the implant with the operating instrument is introduced using a trocar, and the implant then has to be guided laterally around the nerve structures of the vertebral canal.

This pivoting movement is achieved by the fact that the securing piece, on which the implant is screwed firmly on the operating instrument, is rotatable or pivotable relative to the proximal end of the handle. This can be achieved by the fact that the securing piece is rigidly connected to a toothed wheel portion that can be rotated or pivoted by means of a toothed rail.

An actuation of the toothed rail, which is secured on the handle of the operating instrument, thus has the effect that the toothed rail engages in the teeth of the toothed wheel portion and rotates/pivots the latter slightly, as a result of which the implant rigidly connected to the toothed wheel portion is likewise pivoted out from the original position.

This permits simple and safe handling of the implant during the operation, since only one operating instrument is needed which permits both the fixing on the operating element and also the pivoting and the expansion.

After the implant has been introduced into the intervertebral defect or corporectomy defect, expansion is carried out until mechanically stable anchoring and, if appropriate, positional correction have been achieved. The achieved expansion can be modified at any time during the operation, in order to carry out possible repositioning or to reverse an overexpansion of the spinal column segment by actuation of the bevel wheel gear on the operating instrument. Without actuation of the worm gear, however, the implant remains safely in the expanded position as a result of friction and, after the desired expansion has been reached, can then be secured by a fixing screw.

On account of the stability of the implant afforded by the triple columns, it is possible to choose the surface area, the angle degrees and also the surface configuration of the upper and lower plates relatively freely and thereby optimize the form fit and counteract the undesired sinking of the implants.

The implant according to the invention can of course also have three threads coupled to each other, wherein the pitch of each thread is different from that of the other two threads.

The implant according to the invention is preferably made from pure titanium or a titanium alloy such as $Ti_6Al_4$, tantalum, Nitinol, a plastic such as polyether ether ketone (PEEK), or other materials that are suitable as implant materials.

The implant according to the invention is implanted as follows:

With the patient lying on his front, on his side or on his back, the intervertebral space is exposed via a dorsal or ventral abdominal or thoracic approach and is then completely excavated. If a vertebral body is to be removed, this procedure is repeated on the second adjoining intervertebral disc, and the corporectomy is then performed. Depending on the indication, either only parts of the vertebral body can be resected or all parts of the vertebral body can be removed from the spinal canal, including the posterior margin and, if appropriate, bone fragments. The end plates of the anchor vertebrae then have cartilage removed and are roughened in order to stimulate growth of bone into and through the hollow spaces of the implant.

The implant chosen with a suitable size and shape is then introduced into the excavated defect by means of the operating element according to the invention, a combined holding, pivoting, expanding and locking instrument, and is expanded. The geometry of the implant and of the operating instrument permits insertion from the front, from both sides, and also from the rear to the side of the spinal cord sac. The surgical approach can be conventional and open, but it can also be made using a minimally invasive technique. The advantage of a symmetrical introduction of relatively strong expansive and thus corrective forces is afforded particularly in the keyhole technique.

Since the size and configuration of the end plates can be combined relatively freely with the two extension bodies, a large support surface can likewise be used in osteoporosis, and a small one in cases of vertebral fractures where parts of the vertebral body can be preserved.

During the expansion, an edge optionally mounted on the inner cylinder leads to a trimming of the end plate of the anchor vertebra not required for the support and thus means that the end plate that is more difficult to access does not have to be trimmed in a separate work step.

The position is then monitored by intraoperative imaging, mostly by radioscopy. If the position of the implant is less than optimal, the gear rod with the worm gear is rotated in the opposite direction and the implant is thus closed together, repositioned and then expanded again.

The implant can be filled with bone (e.g. spongy bone) or other bone substitute materials (calcium phosphate preparations). The reconstruction of the anterior column is thus complete. Combination with dorsal stabilization is highly recommended especially in the thoracolumbar and lumbar region. Depending on the quality of the bone and the loss of blood, the patient can be mobilized on the same day.

The invention is described in more detail below on the basis of an illustrative embodiment.

In the drawing:

FIG. 5 shows a perspective view of the implant from FIG. 1, secured on the operating instrument and pivoted in.

The implant 11 comprises an upper plate 12 and a lower plate 16, of which the outer faces 13, 17 are provided with spikes 14 that serve for anchoring on/in the vertebral support surfaces.

Upper plate 12 and lower plate 16 each extend in the xy direction and are spaced apart from each other in the z direction.

Figure 1:
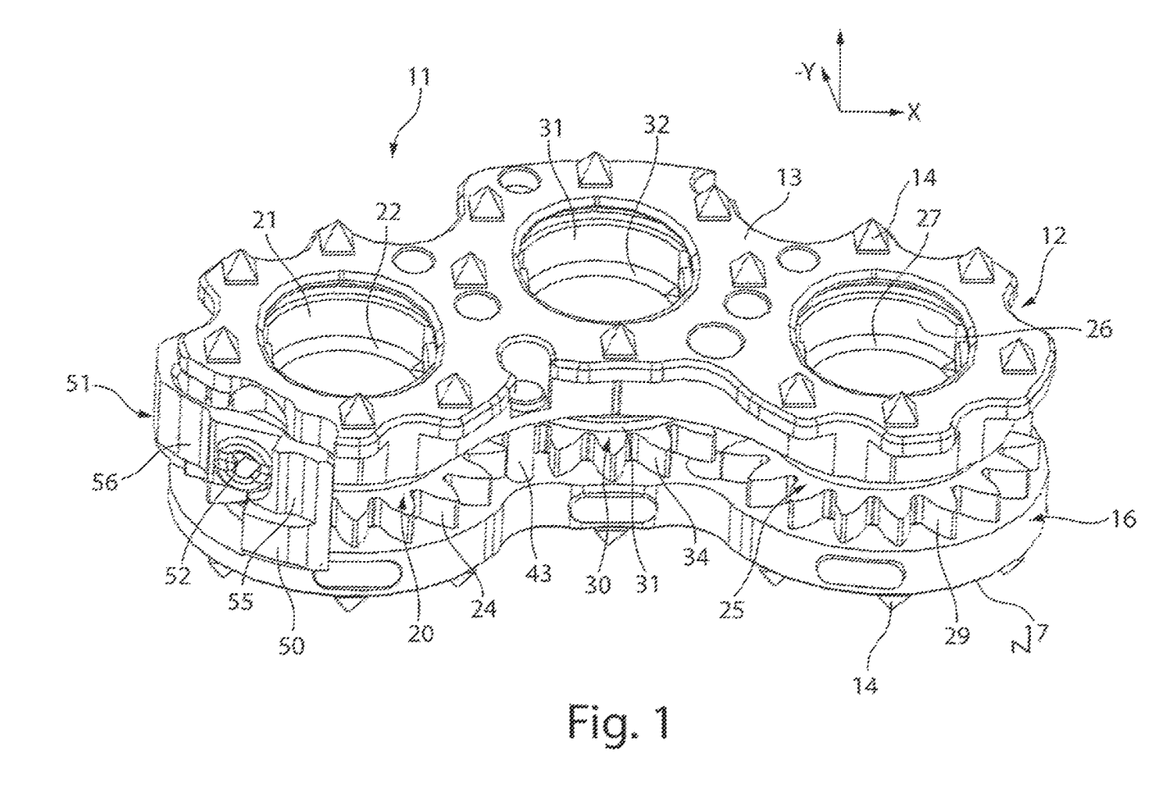
FIG. 1 shows a perspective view of the implant according to the invention at maximum expansion.

The area of the plates 12, 16 of the implant 11 extending in the −y direction, i.e. "rearwards" in FIG. 1, is referred to hereinbelow as "rear area", and the area extending in the +y direction is referred to as "front area".

Between the upper plate 12 and the lower plate 16 there are three gears 20, 25, 30, by means of which the lower plate 16 is movable relative to the upper plate 12, i.e. the implant can be expanded.

Figure 2:
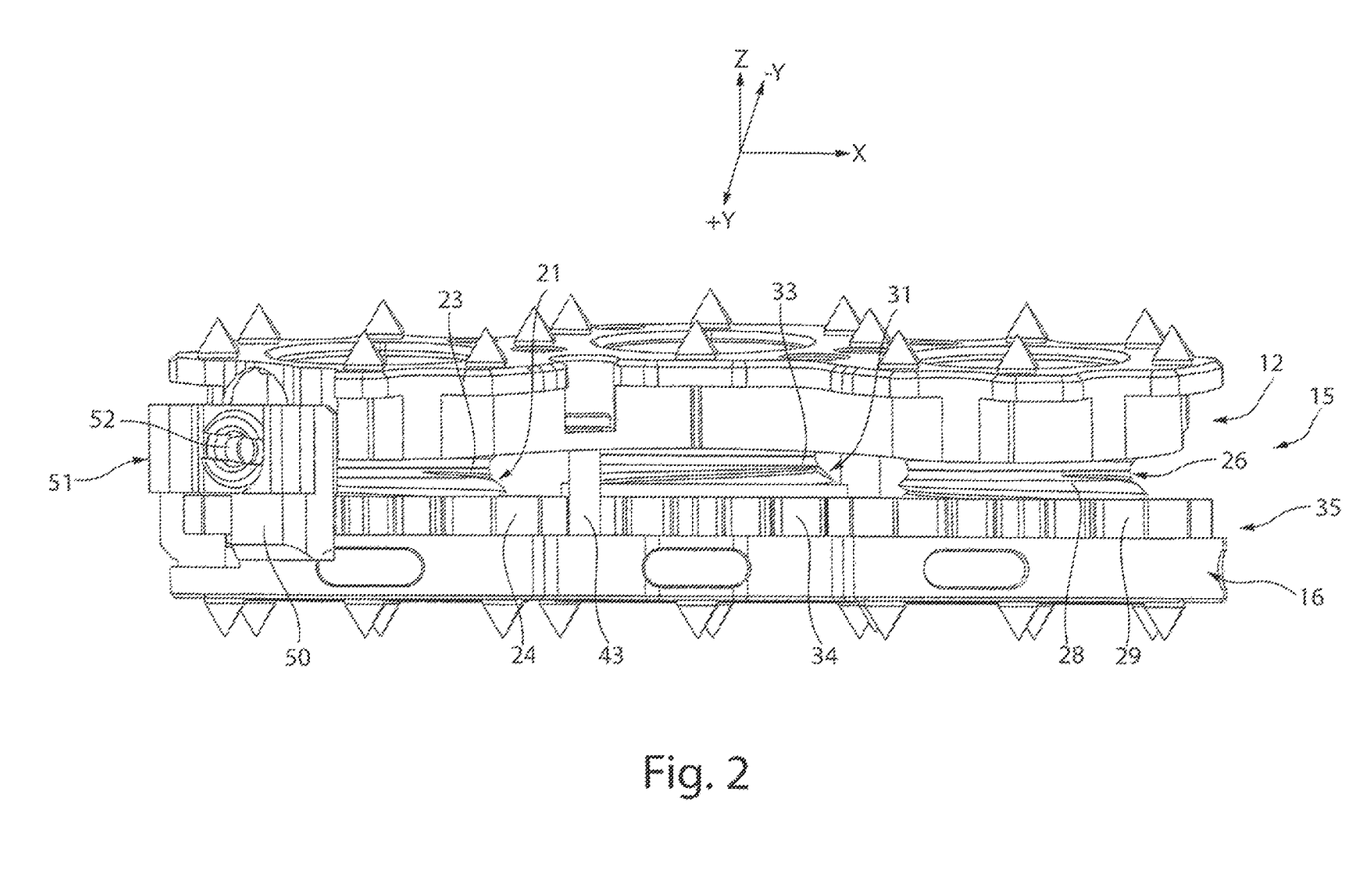
FIG. 2 shows a side of the implant from FIG. 1 in the xz direction.

Each gear 20, 25, 30 consists of a threaded spindle 21, 26, 31 with an outer thread 23, 28, 33 which is guided in a sleeve 22, 27, 32 with inner thread (cf. FIG. 2).

The outer threads 23, 28, 33 of the threaded spindles 21, 26, 31 are spaced apart from each other. The longitudinal axes of the threaded spindles 21, 26, 31 in the z direction extend parallel to each other and are rigidly connected to the upper plate 12, i.e. the three threaded spindles 21, 26 and 31 and the upper plate 12 with the spikes 14 form the upper implant part 15, which is in one piece.

The lower implant part 35 comprises the lower plate 16 with the spikes 14, and the three sleeves 22, 27, 32 that have inner threads and are mounted rotatably in the plate 16.

The inner curved surfaces of the threaded sleeves 22, 27, 32 are provided with threads which form the spindle nuts for the outer threads 23, 28, 33 of the threaded spindles 21, 26, 31.

Each threaded sleeve 22, 27, 32 also has, on its outer curved surface, a drive wheel 24, 29, 34, which is designed as a toothed wheel. The toothed wheels 24, 29, on the threaded sleeves 22, 27, 32 couple the rotation movement of the three threaded sleeves 22, 27, 32.

The threaded sleeves 22, 27, 32 are mounted rotatably in the lower plate 16. When a rotation movement takes place on a toothed wheel 24 of a threaded sleeve 22, the rotation movement is transferred on the one hand to the central threaded sleeve 32 by the meshing of the pairs of toothed wheels 24, 34, and it is also transferred to the threaded sleeve 27 by the further coupling of the pair of toothed wheels 34, 29. These coupled toothed wheels 24, 29, 34 have the effect that the expansion mechanism is driven with a triple adjustment mechanism.

On the other hand, however, the rotation movement on each threaded sleeve 22, 27, 32 also has the effect that a displacement movement of the threaded spindles 21, 26, 31 relative to the threaded sleeves 22, 27, 32 in the z direction takes place, and thus a displacement of the lower plate 16 relative to the upper plate 12, and thus an expansion of the implant 11.

In this way, the expansion of the implant 11, upon rotation of one of the three threaded sleeves 22, 27, 32, takes place in a smooth movement, and jamming of the threads is avoided.

The rotation movement is introduced into the toothed wheel 24 of the threaded sleeve 22 of the gear 20 by virtue of the fact that a toothed wheel 85 of an operating instrument 80 (to be described in more detail below) engages on the toothed wheel 24 of the gear 20 and introduces the rotation movement into the toothed wheel 24.

In the implant 11 according to the invention, the three threads 20, 25, 30, seen in a plan view, are not arranged in a line but instead in the shape of an arc or "C". The two threads 20, 25 lie near the ends of the C, while the thread 30 lies at the centre of the C. The three threads 20, 25, 30 are mirror-symmetrical with respect to the yz axis. In the plan view (in the −z direction), the three threads 20, 25, 30 are arranged in the form of a flat isosceles triangle.

If the central thread 30 has a different pitch than the two end threads 20, 25, this arrangement of the threads and the likewise arc-shaped (C-shaped) form of the plates 12, 16 mean that, during the expansion, it is also possible to obtain a slight tilting of the upper plate 12 relative to the lower plate 16.

The pitches of the outer threads 23, 28 of the threaded spindles 21, 26 and the corresponding inner threads of the threaded sleeves 22, 27 are equal and smaller than the pitch of the central gear 30, namely the outer thread 33 of the threaded spindle 31 and the corresponding inner thread of the threaded sleeve 32.

Figure 3:
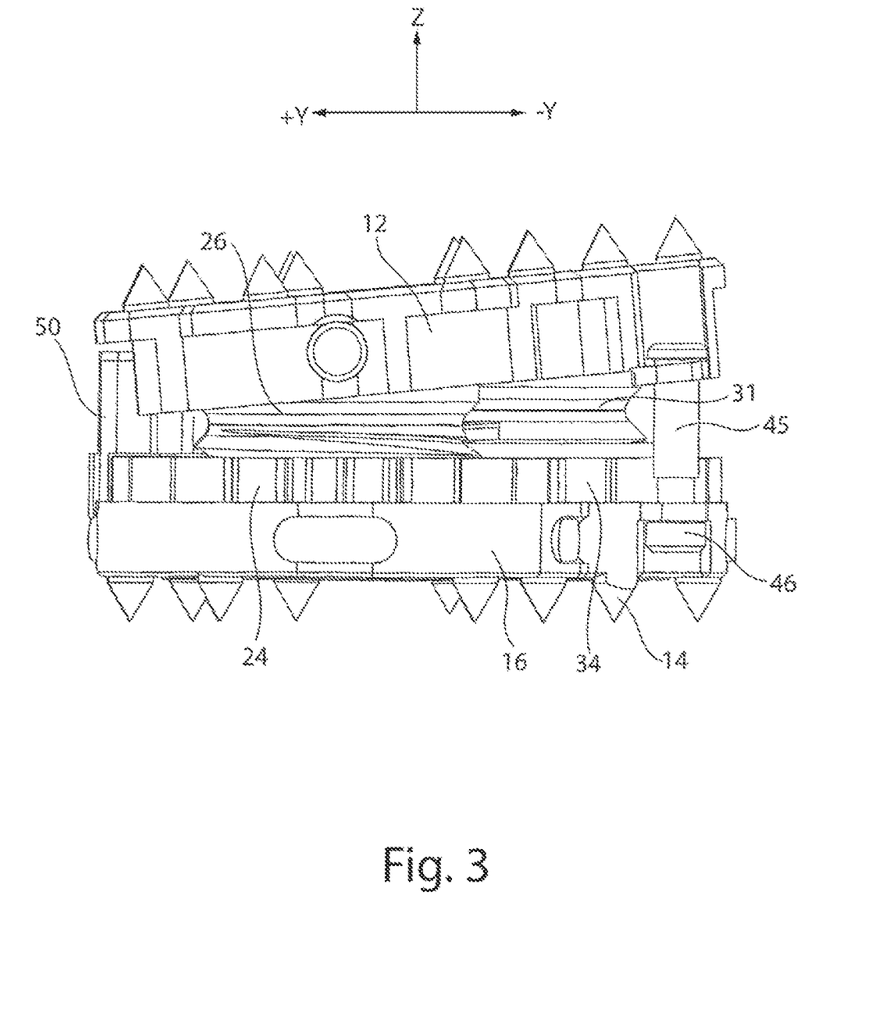
FIG. 3 shows a side view of the implant from FIG. 1 in the yz direction.

The different thread pitches mean that, during the expansion, the upper plate 12 is lifted less strongly in the front area (area in the +y direction in FIG. 1) than in the rear area of the implant 11 (area in −y direction in FIG. 1), i.e. the distance between the upper plate 12 and the lower plate 16 of the implant 11 is greater at the plate end in the −y direction than at the plate end in the +y direction, i.e. the two plates 12, 16 are slightly "tilted" relative to each other and thus have a lordosis shape (cf. in particular FIG. 3).

In a preferred embodiment, the pitches of the threads 23, 22, 28, 27 of the two outer gears 20, 25 are each 1.0 mm, and the pitch of the central gear 30 is 1.25 mm. However, the pitches can of course also be different from this.

Figure 4:
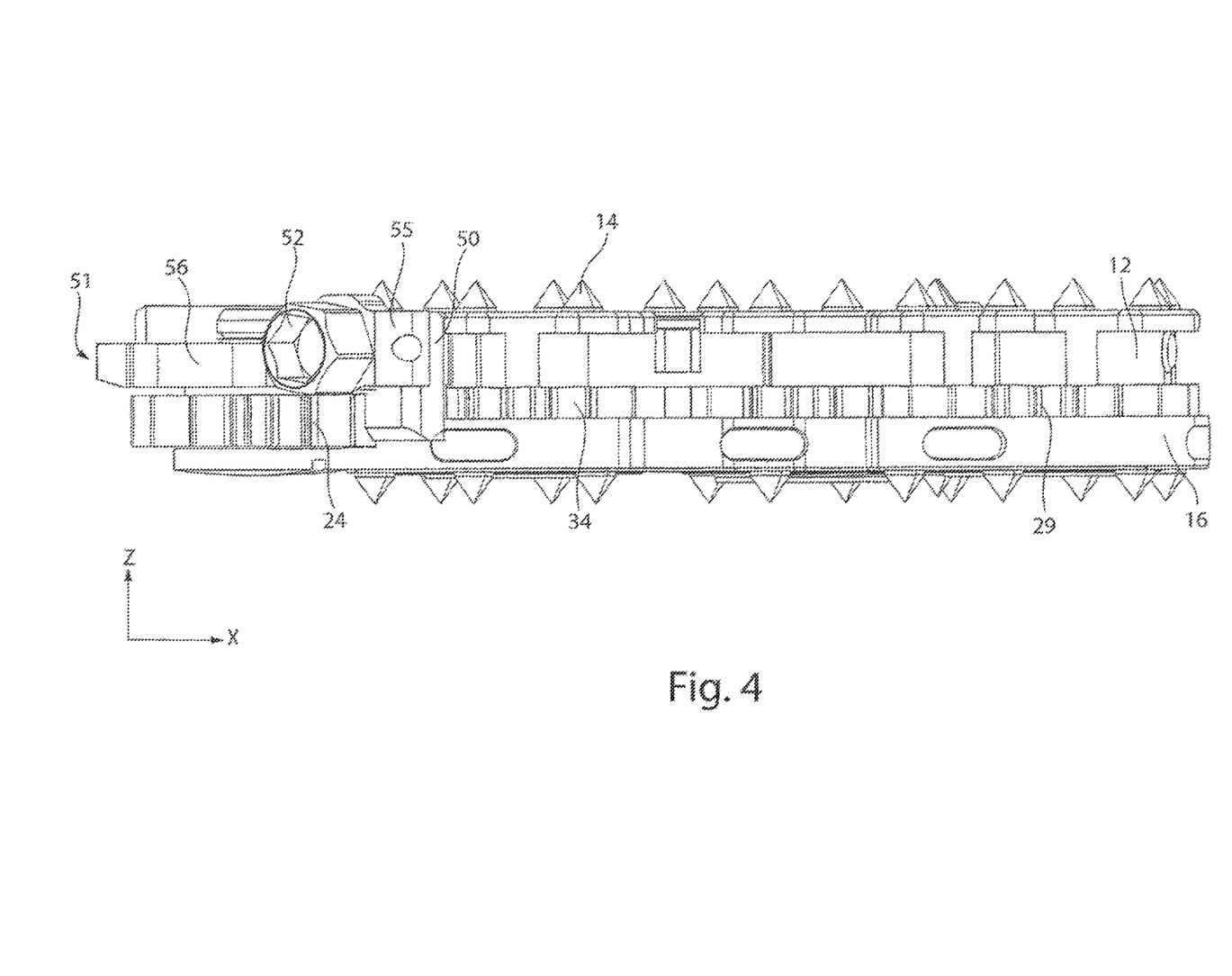
FIG. 4 shows the implant from FIG. 2, but in the non-expanded state.

In the non-expanded state (FIG. 4), the distances in the z direction between the upper plate 12 and the lower plate 16 are the same all over, i.e. the planes of the plates 12, 16 extend parallel to each other. A pin 43, 45 with a limit stop 44, 46 is arranged parallel to the longitudinal axes (z direction) of the threaded sleeves and spindles 21, 22, 26, 27, 31, 32 near the central thread 30 in the "rear" area (i.e. in the −y direction) and in the front area (i.e. in the +y direction), wherein each pin 43, 45 with limit stop passes through a respective bore in the upper plate 12 and lower plate 16. At maximum expansion, the head ends of each pin 43, 45 bear on the top face of the upper plate 12 and the limit stops 44, 46 bear on the underside of the lower plate 16, i.e. the pins 43, 45 and limit stops 44, 46 define the expansion movement and additionally serve as a guide.

Since the expansion in the +z direction in the front area, i.e. in the +y direction, is smaller than in the rear area, i.e. in the −y direction, the pin 43 in the rear area is also longer than the pin 45 in the front area.

Two vertically extending portions 50 are provided on the lower plate 16, adjacent to the gear 20, and are rigidly connected to each other via a horizontal portion 51 with a threaded bore 52. The threaded bore 52 serves to secure a screw 78 provided on the proximal end of the operating instrument 80.

The lower plate 16, the two vertical portions 50 and the horizontal portion 51 form a rigid unit. The thickness of the upper and lower plates 12, 16 is relatively small. In addition, the threaded sleeves 22, 27, 32 and the threaded spindles 21, 25, 31 are secured in the plates 12, 16 and pass through these, and each gear consists exactly of one sleeve 22, 27, 32 and one spindle 21, 25, 31. A compact structure with maximum lift is thus obtained.

The upper and lower plates 12, 16 of the implant can have openings through which anchoring screws can be screwed obliquely into the adjacent vertebrae.

At both sides of the threaded bore 52, the horizontal portion 51 has two slightly curved surfaces 55, 56, which serve to position the corresponding surfaces 81, 82 of the securing piece 77 (cf. FIG. 9) at the proximal end of the operating instrument. In this way, with the screw fixed, the implant is rigidly connected to the operating instrument.

The end faces of the threaded sleeves 22, 27, 32 and sleeve-shaped threaded spindles 21, 26, 31 are open, i.e. not covered by the upper plate 12 or lower plate 16. The implant 11 thus has three tubular through-openings extending from the outer face 13 of the upper plate 12 to the outer face 17 of the lower plate 16.

Figure 5:
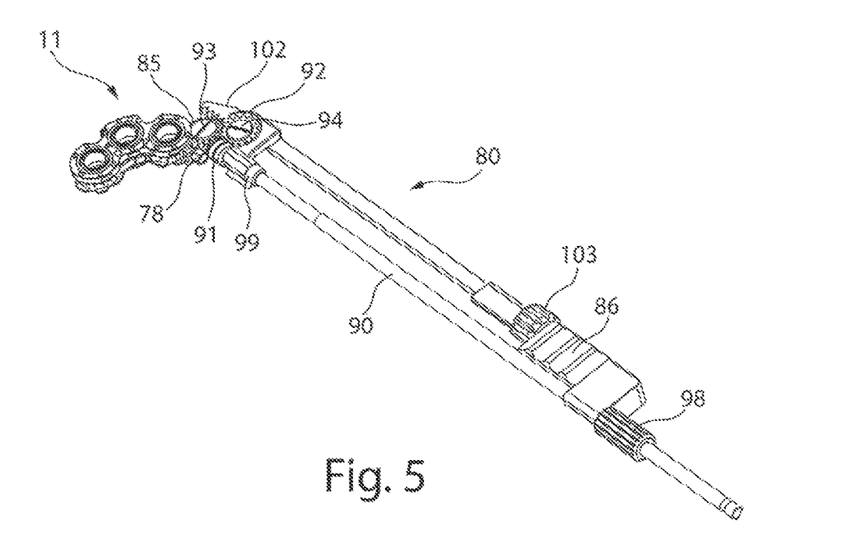
Figure 6:
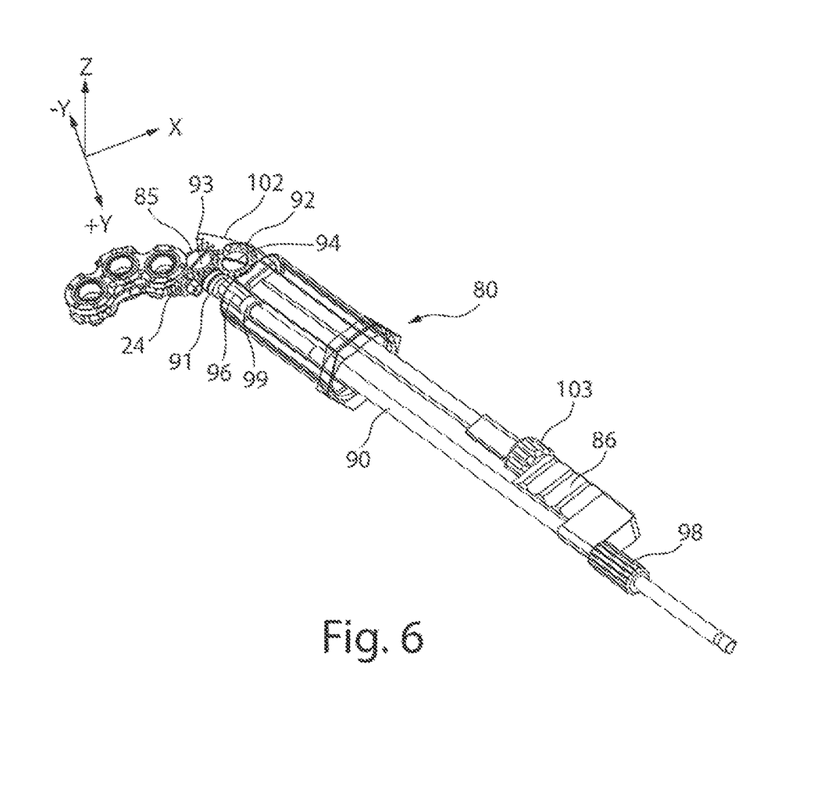
FIG. 6 shows the operating instrument with pivoted-in implant from FIG. 5 with trocar.

The implant is operated with an instrument 80, which is shown in detail in FIG. 5 ff. The instrument 80 serves both for the securing, screwing in, pivoting in and insertion of the implant 11 and also for the expansion and the fixing of the expansion position.

In order to secure the implant 11 safely on the operating instrument 80 for the subsequent handling, i.e. insertion, positioning, pivoting in and expansion, the instrument 80 is screwed, by means of a locking screw 78 at the proximal end of the operating instrument 80, into the threaded bore 52 of the horizontal portion 51 of the implant 11.

Figure 9:
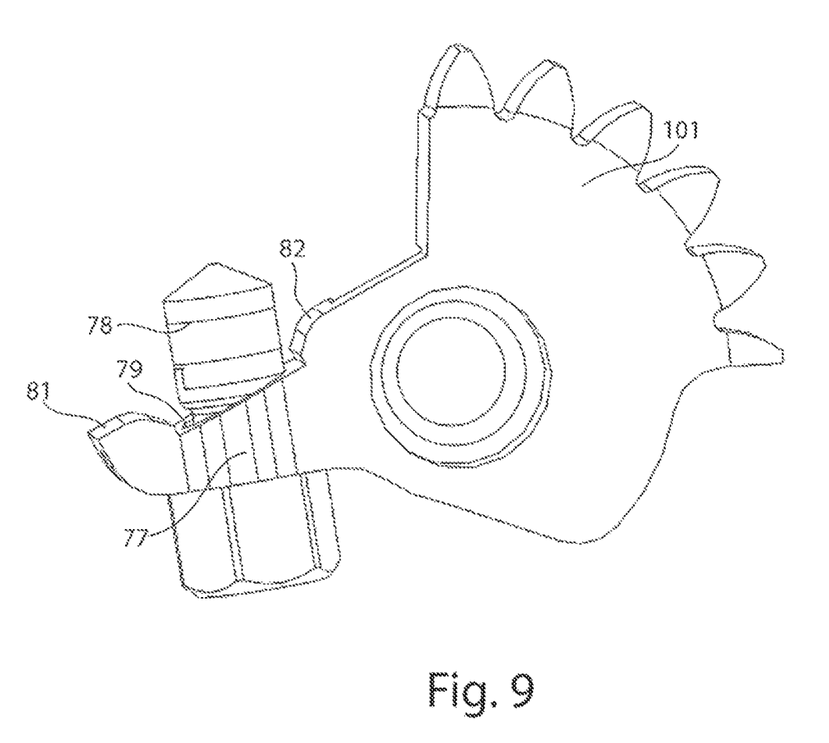
FIG. 9 shows the toothed wheel portion of the operating element.

The locking screw 78 is secured non-detachably in a screw thread 79 in a securing piece 77. The securing piece 77 is rigidly connected to the toothed wheel portion 101 described in more detail below (FIG. 9).

The positioning surfaces 81, 82 adjacent to the screw thread 79 correspond to the positioning surfaces 55, 56 adjacent to the screw thread 52, such that the implant 11 is secured rigidly with a form fit on the operating instrument 80.

By screwing the implant 11 to the proximal end of the operating instrument 80, not only is a rigid connection between implant 11 and operating instrument 80 achieved, and thus precise insertion, but also at the same time the toothed wheel 85 located at the proximal end of the operating instrument 80 is brought into engagement with the toothed wheel 24 of the implant. The toothed wheels 85, 24 lie in one plane (xy plane), and the teeth of the wheel 85 engage laterally in the teeth of the drive wheel 24.

The rotation movement of the toothed wheel 85 takes place through rotation of the distal end of a gear rod 90, at the proximal end of which there is a worm drive 91, of which the rotation movement is transferred by means of a further toothed wheel 92 to the toothed wheel 85, which drives the toothed wheel 24 of the implant 11.

The toothed wheels 85, 92 lie in one plane. The worm drive 91 engages laterally on the outwardly pointing teeth of the toothed wheel 92.

By means of this arrangement, a rotation movement of the toothed wheel 85 can be introduced at the proximal end even in the case of a slender configuration of the proximal end of the operating instrument 80.

The gear rod 90 is mounted rotatably in the handpiece 86, specifically in such a way that the gear rod 90 is received in a respective seat 96, 97 in the handpiece 86 near the proximal and distal ends of the rod 90. The rod 90 is secured against falling out by means of the worm drive 91 having a greater circumference than the seats 96, 97, and by means of a limit stop 99 near the proximal end of the operating instrument 80, and by means of the grip 98 at the distal end.

The toothed wheels 85, 92 are mounted rotatably with screws 93, 94 in the handpiece 86. The toothed wheel 92 is much larger than the toothed wheel 85.

Figure 7:
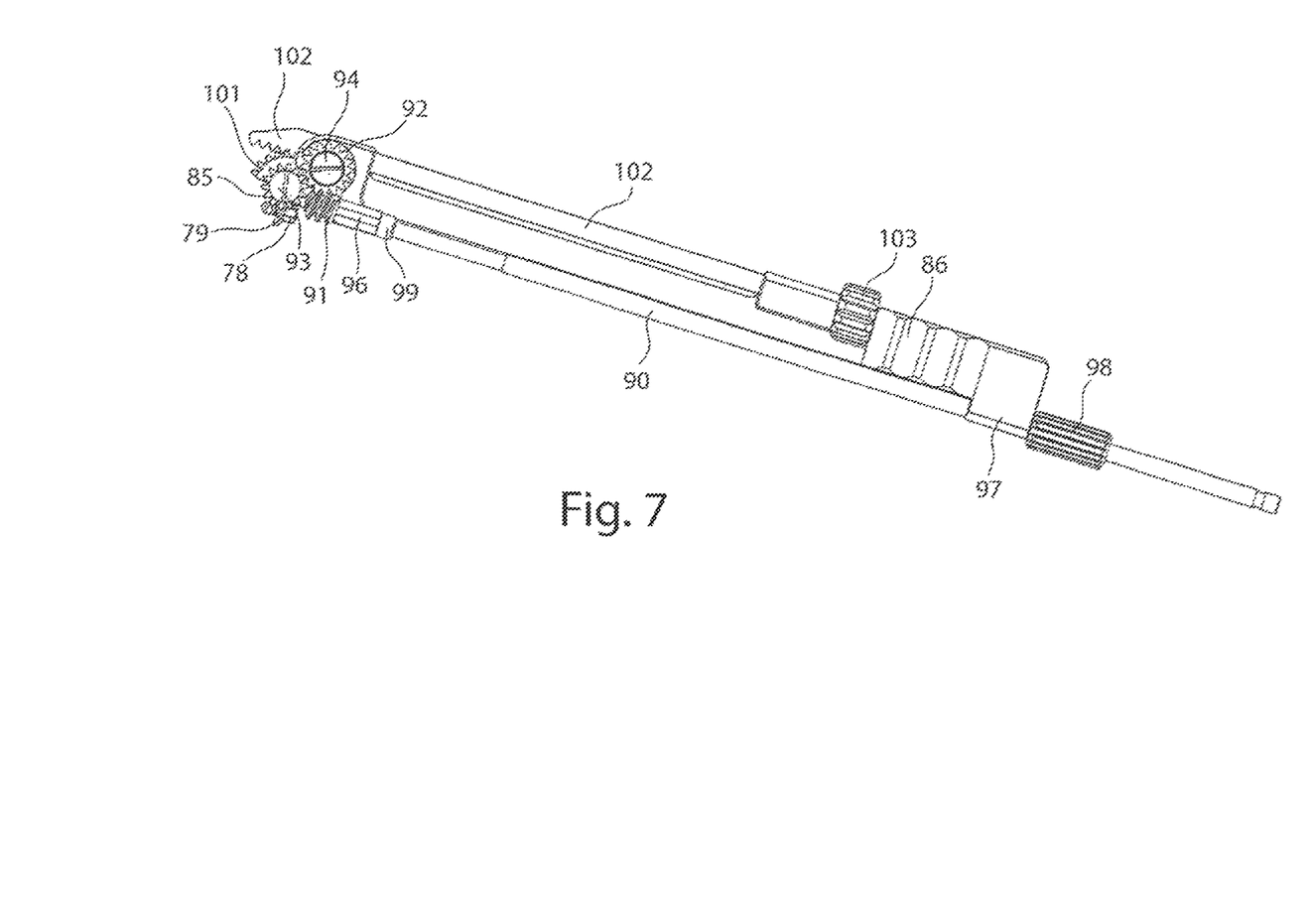
FIG. 7 shows a view of the operating instrument in the xy direction from above (+z direction)
Figure 8:
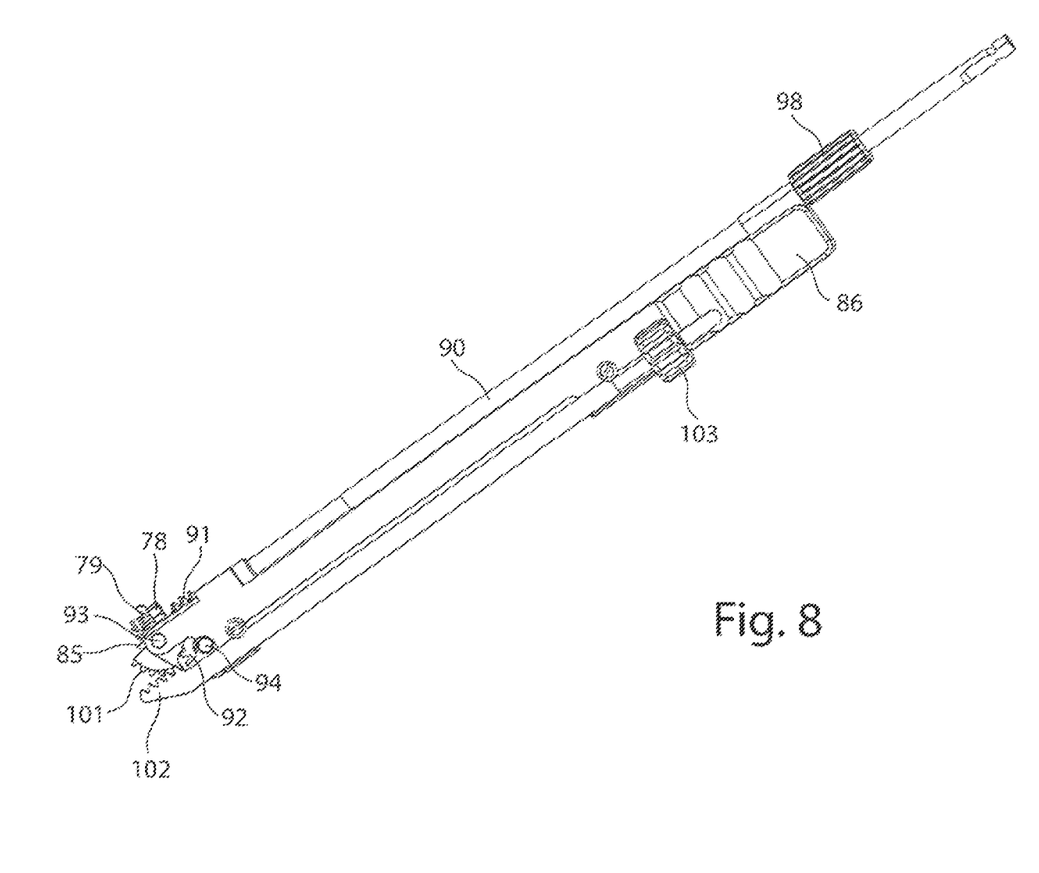
FIG. 8 shows a view of the operating instrument in the xy direction from below (−z direction)

In the plan view shown in FIG. 7, the head of the screw 93 lies above the toothed wheel 85. The shank of the screw 93 passes through a bore in the toothed wheel 85. Under the toothed wheel 85, a toothed wheel portion 101 is provided through which the thread of the screw 93 likewise passes (cf. FIG. 8).

When the toothed wheel portion 101 is turned, the portion 101, along with the securing piece 77 connected thereto and also the screw thread 79, is rotated on a circular path about the axis of rotation of the toothed wheel 85, i.e. the shank of the screw 93. Upon actuation of the toothed wheel portion 101, an implant 11 screwed firmly onto the operating instrument 80 can thus be pivoted on a circular path about the toothed wheel 85. In other words, during a rotation movement of the toothed wheel portion 101, the implant 11 at the proximal end of the operating instrument 80 is rotated about the toothed wheel 85 or the screw 93.

The rotation movement of the toothed wheel portion 101 takes place via a toothed rod 102, which is held in the handpiece 86 and which can be moved forwards and backwards via a knurled screw 103.

A forward movement of the toothed rod 102 causes a forward movement of the toothed wheel portion 101 and therefore a rotation movement of the toothed wheel portion 101 and thus a pivoting of the implant 11.

The longitudinal axes of the rod 90, of the toothed rod 102 and of the handpiece 86 extend parallel to each other.

The invention claimed is:

1. A combination of an expandable implant and an operating instrument, the expandable implant comprising an upper plate and a lower plate which extend in the xy plane and which serve for anchoring on/in vertebral support surfaces, the expandable implant further comprising at least three gears which are coupled to each other, wherein the gears serve to expand the expandable implant, each gear having a threaded spindle and a threaded sleeve with corresponding inner thread, wherein the pitch of one thread is different from the pitch of the other threads, the operating instrument being engageable with the expandable implant for use in expanding the expandable implant, the operating instrument comprising a handpiece having a longitudinal axis, a gear drive connected to the handpiece for driving one of the gears of the expandable implant, means for securing the gear drive to the expandable implant, and means for moving the expandable implant laterally relative to the longitudinal axis of the handpiece while keeping the handpiece stationary, wherein the moving means comprises a rotatable toothed wheel portion and wherein the rotatable toothed wheel portion is driven by an actuation rod.

2. The combination according to claim 1, characterized in that the gears, in a plan view (z direction), are arranged on an arc of a circle or in a C shape.

3. The combination according to claim 1, characterized in that two end gears have a different pitch than a central gear.

4. The combination according to claim 3, characterized in that the two end gears have a smaller pitch than the central gear.

5. The combination according to claim 1, characterized in that drive wheels are provided on each threaded sleeve and are coupled to each other.

6. The combination according to claim 1, characterized in that the expandable implant has a portion with a threaded bore for screwing on the operating instrument.

7. The combination according to claim 1, characterized in that the operating instrument further comprises a worm drive and a first toothed wheel, in that the worm drive drives the first toothed wheel, in that the first toothed wheel drives the gear drive, and in that the first toothed wheel and the gear drive lie in one plane.

8. The combination according to claim 1, characterized in that the actuation rod is driven via a knurled screw.

* * * * *